US008775353B2

(12) United States Patent
Acquisti et al.

(10) Patent No.: US 8,775,353 B2
(45) Date of Patent: Jul. 8, 2014

(54) VALIDATING LEGITIMACY OF A SOCIAL SECURITY NUMBER OR OTHER IDENTIFIER

(75) Inventors: Alessandro Acquisti, Pittsburgh, PA (US); Ralph Gross, Pittsburgh, PA (US); Ioanis Alexander Biternas Wischnienski, San Francisco, CA (US)

(73) Assignee: Carnegie Mellon University, Pittsburgh, PA (US)

( * ) Notice: Subject to any disclaimer, the term of this patent is extended or adjusted under 35 U.S.C. 154(b) by 394 days.

(21) Appl. No.: 13/177,157

(22) Filed: Jul. 6, 2011

(65) Prior Publication Data
US 2012/0173473 A1 Jul. 5, 2012

Related U.S. Application Data

(60) Provisional application No. 61/399,048, filed on Jul. 6, 2010.

(51) Int. Cl.
| | |
|---|---|
| *G06F 17/00* | (2006.01) |
| *G06N 5/02* | (2006.01) |
| *G06F 9/44* | (2006.01) |
| *G06N 7/02* | (2006.01) |
| *G06N 7/06* | (2006.01) |
| *G06F 21/33* | (2013.01) |
| *G06Q 50/26* | (2012.01) |
| *G06F 21/45* | (2013.01) |
| *G06Q 40/02* | (2012.01) |
| *G06F 21/64* | (2013.01) |
| *G06Q 50/22* | (2012.01) |

(52) U.S. Cl.
CPC ............... *G06F 21/45* (2013.01); *G06F 21/33* (2013.01); *G06Q 50/265* (2013.01); *G06Q 40/02* (2013.01); *G06F 21/645* (2013.01); *G06Q 50/22* (2013.01)
USPC ............................................ 706/47; 706/52

(58) Field of Classification Search
None
See application file for complete search history.

(56) References Cited

U.S. PATENT DOCUMENTS

| | | | |
|---|---|---|---|
| 5,946,681 A * | 8/1999 | Shorter ................................ 1/1 |
| 6,968,348 B1 * | 11/2005 | Carone et al. ................. 707/696 |
| 2004/0215557 A1 * | 10/2004 | Michelsen ...................... 705/39 |
| 2005/0005113 A1 * | 1/2005 | Dillon et al. .................. 713/168 |

OTHER PUBLICATIONS

Gross, Ralph, and Alessandro Acquisti. "Information revelation and privacy in online social networks." Proceedings of the 2005 ACM workshop on Privacy in the electronic society. ACM, 2005.*
Torra, Vicenc. "OWA operators in data modeling and reidentification." Fuzzy Systems, IEEE Transactions on 12.5 (2004): 652-660.*

(Continued)

*Primary Examiner* — Ben Rifkin
*Assistant Examiner* — Daniel Pellett
(74) *Attorney, Agent, or Firm* — Downs Rachlin Martin PLLC (57) ABSTRACT

Methods and systems for predicting statistically probable systematically assigned identifiers are disclosed, as are methods and systems for determining the likelihood that a systematically assigned identifier provided by a purported assignee of the identifier is legitimate. In one example, determining the likelihood of legitimacy includes determining the likelihood that the provided identifier is a valid identifier and determining the likelihood that the provided identifier was assigned to the purported assignee. To accomplish this validation, the present disclosure employs patterns of assignment discernable for systematically assigned identifiers in combination with statistical methods.

68 Claims, 5 Drawing Sheets

(56) References Cited

OTHER PUBLICATIONS

Torra, Vicenç, and Josep Domingo-Ferrer. "Record linkage methods for multidatabase data mining." Information fusion in data mining. Springer Berlin Heidelberg, 2003. 101-132.*

Clifton, Chris, and Don Marks. "Security and privacy implications of data mining." ACM SIGMOD Workshop on Research Issues on Data Mining and Knowledge Discovery. 1996.*

Wessmiller, R. "Using Audit Software and the Death Master File to Catch Crooks." Information Systems Control Journal 4 (2003): 49-50.*

Domingo-Ferrer, Josep, and Vicenç Torra. "Validating distance-based record linkage with probabilistic record linkage." CCIA 2 (2002): 207-215.*

\* cited by examiner

VALIDATING LEGITIMACY OF A SOCIAL SECURITY NUMBER OR OTHER IDENTIFIER

RELATED APPLICATION DATA

This application claims the benefit of priority of U.S. Provisional Patent Application Ser. No. 61/399,048, filed on Jul. 6, 2010, and titled "Predicting and Validating Social Security Numbers from Public Data," which is incorporated by reference herein in its entirety.

FIELD OF THE INVENTION

The present invention generally relates to the field of identity verification. In particular, the present invention is directed to validating legitimacy of a social security number or other identifier.

BACKGROUND

In information-based economies, sensitive and/or valuable information may be available through transactions relying on systematically assigned identifiers. The identifiers can identify financial accounts, persons, personal property (e.g., a VIN number used to uniquely identify an automobile), transaction records (e.g., medical records), and many other sources of information.

One example of such an identifier is a Social Security Number (SSN), issued to citizens, permanent residents, or temporary residents of the United States by the Social Security Administration. Originally created as an identifier for an account tracking an individual's earnings, the SSN is now frequently used as an identifier to verify the identity of an individual. Identity verification using an SSN may be required, for example, when applying for credit, opening a bank account, verifying immigration status, seeking health care, and many other transactions critical to participation in a modern economy. As such, the SSN is commonly sought by identity thieves or falsified as part of fraudulent activities.

SUMMARY OF THE DISCLOSURE

In one implementation, the present disclosure is directed to a method of validating a provided Social Security Number purported to be associated with a person. The method includes receiving the provided Social Security Number; predicting a set of statistically probable Social Security Numbers; comparing the provided Social Security Number to the set of statistically probable Social Security Numbers so as to determine a likelihood that the provided Social Security Number is legitimate; and communicating the likelihood to a reviewer.

In another implementation, the present disclosure is directed to a machine-readable storage medium containing machine-executable instructions for performing a method of validating a provided Social Security Number purported to be associated with a person. The machine-executable instructions include a first set of machine-executable instructions for receiving the provided Social Security Number; a second set of machine-executable instructions for predicting a set of statistically probable Social Security Numbers; a third set of machine-executable instructions for comparing the provided Social Security Number to the set of statistically probable Social Security Numbers so as to determine a likelihood that the provided Social Security Number is legitimate; and a fourth set of machine-executable instructions for communicating the likelihood to a reviewer.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Aspects of the present disclosure include methods, software, and systems for verifying legitimacy of a systematically assigned identifier that has been provided or acquired as part of a process to confirm identity. Systematically assigned identifiers contemplated by the present disclosure can include, but are not limited to, identifiers identifying property (tangible and intangible personal property), transactions, as well as persons. For example, identifiers identifying property can include a vehicle identification number, a vehicle operator license number, a financial account number, a credit card or debit card number, a financial transaction routing number, a government issued license number, and many others. Examples of identifiers identifying an individual can include any of the foregoing (which may be used as a substitute for identifying a person), as well as, for example, a social security number. Those skilled in the art will appreciate that other systematically assigned identifiers not expressly described but consistent with the present disclosure may also be used.

Methods and systems of the present disclosure may be applied to many formats of identifiers. For example, identifiers contemplated by the present disclosure can use any type or combination of alpha-numeric characters or symbols and are not limited merely to strings of numbers, or strings of letters. Indeed, combinations of numbers, letters, and even symbols can be readily used to create a systematically assigned identifier. Furthermore, alpha-numeric identifiers are not limited to Roman characters but also include, for example, Cyrillic, Greek, and Arabic alpha-numeric characters. Those skilled in the art will appreciated that these are but a small sample of the alphabets, character-types, and symbols that can be used to create a systematically assigned identifier.

As mentioned above, examples discussed in the present disclosure apply to those identifiers that have been assigned using a systematic assignment methodology. This systematic methodology may include virtually any basis or bases forming the system of assignment from which an identifier is assigned. For example, identifiers may be assigned using any one or more of the following bases that are a function of the entity assigning the identifier: assignment date, assignment source (e.g., a state, a governmental unit, a non-governmental entity, a branch, a unit or sub-unit of an assigning entity, etc.), and others. In other examples, identifiers may be assigned by using values associated with any one or more of the following bases that are a function of the entity being assigned the identifier (hereinafter the "assignee"): birth date, fabrication date, importation date, physical features (e.g., color, make, model), location of birth, location of fabrication, type of assignee (gender, race, ethnicity, model, type, etc.), or level of service provided (e.g., membership type, premium paid to entity assigning identifier, etc.). Those skilled in the art will appreciate that these bases are but a small portion of the bases that can be used to systematically assign an identifier, to which the methodologies of the present disclosure apply.

Also, consistent with the broad definition of basis previously described, the term "value" used in the present disclosure to describe a specific entry of one or more bases, is defined so as to include more than merely a numeric value. For example, because the term "basis" can include location of birth, a value of the location of birth can be a zip code, a state name, a state abbreviation, a town, or a town and state combination. In other examples, for example the level of service provided to a member of an organization, the values may include "premium" or "standard," or abbreviations thereof. Indeed, the term "value" as used herein includes any appropriate descriptor or representation of one or more bases, whether numeric or not, used to systematically assign an identifier.

Prediction and Validation of a Generic Identifier

Figure 1:
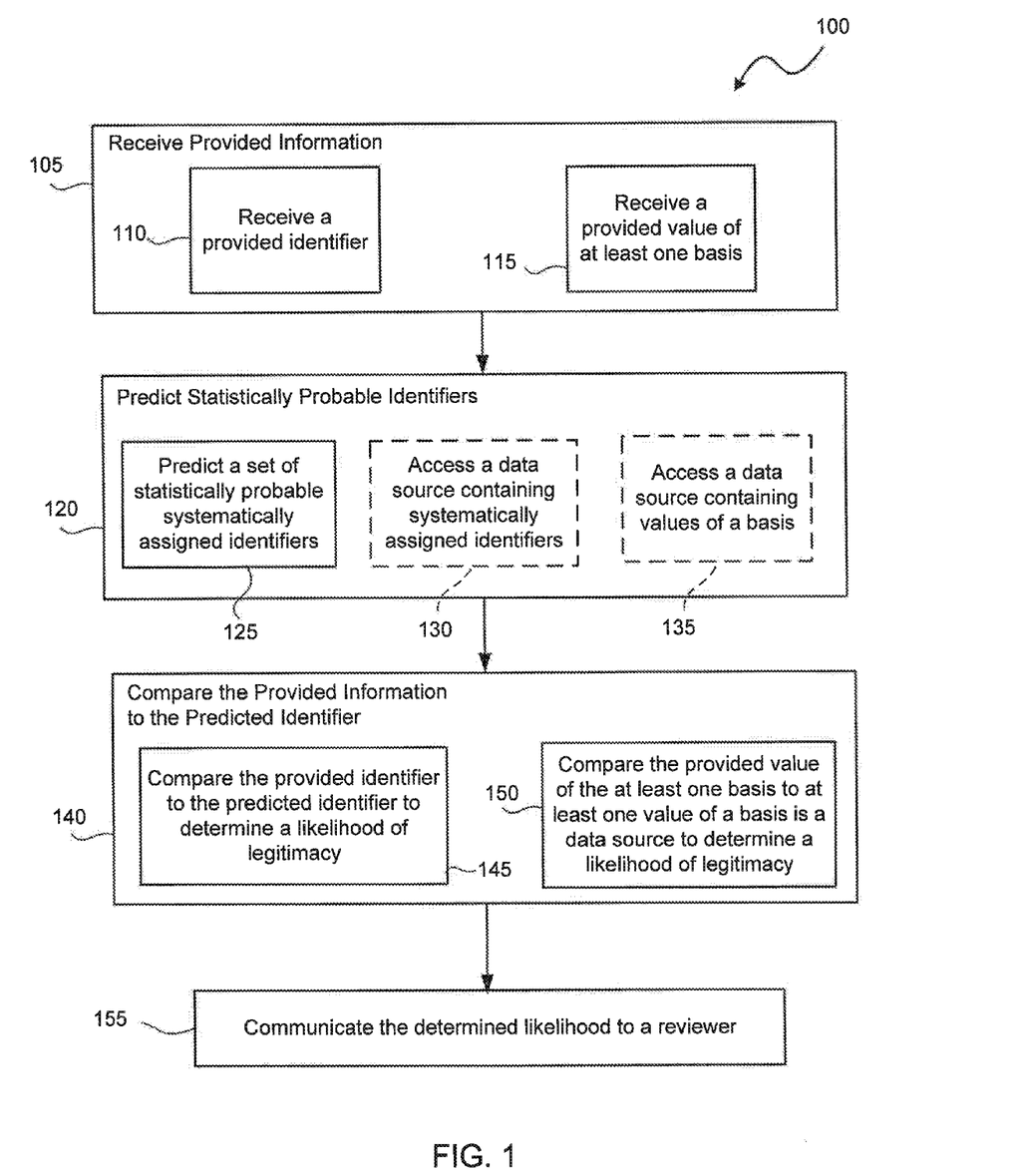
FIG. 1 is a flow diagram depicting an exemplary embodiment of a method used to validate a provided identifier.
Figure 2:
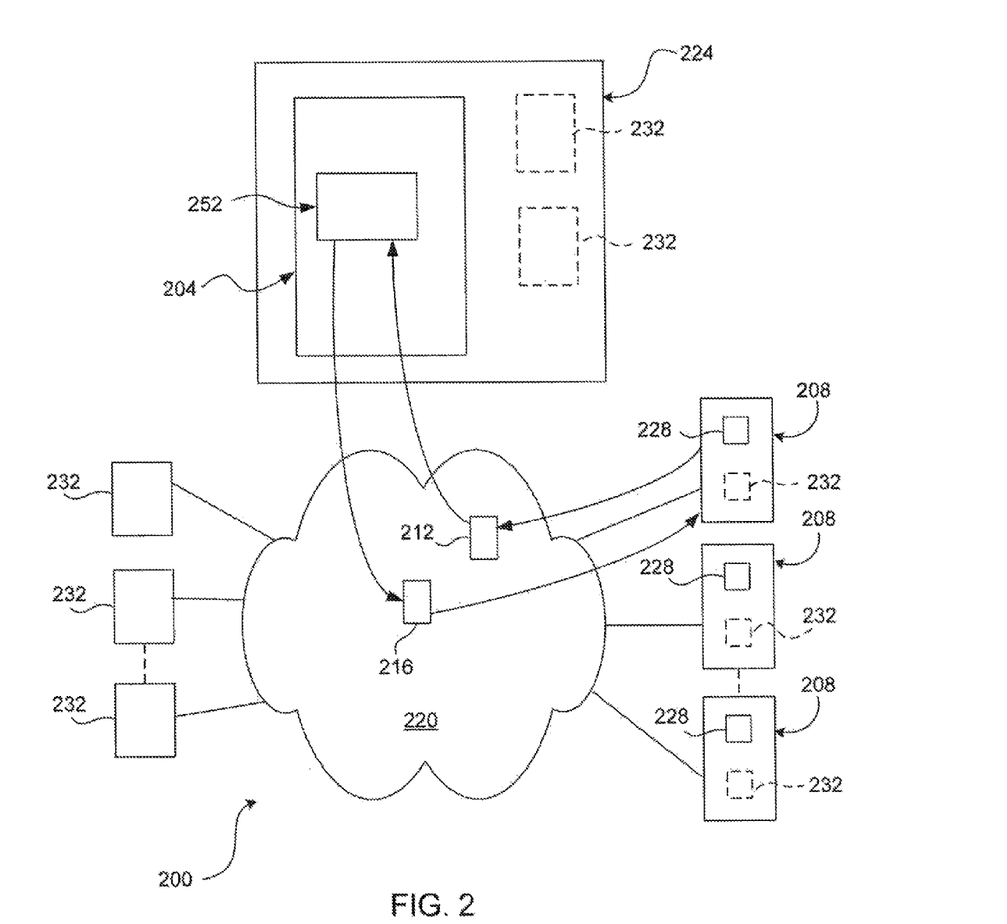
FIG. 2 is a high-level diagram of an identifier-validating-system in an exemplary operating environment.

Turning now to the drawings, FIG. 1 depicts an exemplary method 100 that contains steps for validating the legitimacy of a provided systematically assigned identifier. Following the discussion of FIG. 1, a discussion of FIG. 2 illustrates an exemplary environment 200 that is suitable for implementing method 100. It is noted here at the outset that environment 200 is used simply for the purposes of illustration. Those skilled in the art will readily appreciate that method 100, as well as other methods implementing various features of the present disclosure, can be implemented in environments other than environment 200. Because such alternative environments are known, it is not necessary to describe or even list other types of environments. That said, where appropriate, some alternatives of various parts and features of environment 200 are presented to give a sense of scope.

In this example, method 100 begins with meta-step 105, which is directed to receipt of information, and which includes two steps, step 110 and step 115, that may be performed in any order. At step 110 a provided systematically assigned identifier requiring validation is received, and at step 115 one or more values of one or more corresponding respective bases used as part of the systematic assignment is received. In this example, as well as other examples throughout the present disclosure, the meaning of the term "validation" includes verifying or determining legitimacy of the identifier. As explained above, the provided identifier received at step 110 can be any one of a wide variety of identifiers that identifies, for example, property, an account, a financial transaction, a transaction routing number, a person or other entity, or other assignees described above. As also explained above, a value of each basis forming the system of assignment received at step 115 can include any one or more of the character types discussed above.

Information received at meta-step 105 can be received by any of a number of receivers. For example, the information can be received by a human receiver such as a clerk, an employee, a legal agent, a law enforcement officer, a government official, or any other human operating in any capacity. In other examples, the information can be received by a computer-based system such as an application-specific database, webpage, or other software, a general purpose database, an optical-recognition system that receives a written identifier into a computer-based application, or any other electronic application as is well known to those skilled in the art.

Continuing with method 100, meta-step 120 includes two steps directed to the prediction of a set of statistically probable systematically assigned identifiers, or portions thereof, that will be used later in the method to evaluate the legitimacy of the provided identifier. At step 125 within meta-step 120, the set of statistically probable systematically assigned identifiers, or portions thereof, can be predicted as part of validating the legitimacy of the provided identifier. This prediction can be accomplished using a wide variety of techniques. For example, a set of probable identifiers, or a set of portions of identifiers, can be calculated using one or more bases of assignment provided at step 115. As an illustration of this example, if one basis of the systematic assignment is an origination date (e.g., a date of birth, an account start-date, an incorporation date, a fabrication date, etc.), a set of statistically probable identifiers, or portions thereof, can be generated based on the value of the origination date provided at step 115. As those skilled in the art will appreciate, there are many other analogous illustrations using different bases corresponding to different systems of assignment.

However, a prediction conducted at step 125 need not necessarily use a basis value provided at step 115. Instead, at step 130, a prediction of legitimacy can be generated using only the characteristics of historical systematically assigned identifiers queryable through a data source. For example, if the frequency of use of selected alpha-numeric or symbolic characters, or their combination, in a population of historical systematically assigned identifiers is known, then a predicted set of most likely identifiers, or portions thereof, will be a function of the most commonly used characters, combinations, and/or subsets of combinations of the most commonly used characters. Characterizing the frequency of use of characters or their combination can be accomplished by accessing a data source that includes historical systematically assigned identifiers, i.e., identifiers actually assigned.

Additionally, or alternatively, at step 135 the prediction of the set of statistically likely identifiers can be informed through accessing a data source that contains the value(s) of the basis or bases provided at step 115 along with corresponding historically assigned identifiers. That is, the received value can be used to facilitate the prediction by, in one example, consulting a data source containing other values of the basis received at step 115 and corresponding historical systematically assigned identifiers. Using a relationship between the received value, others values relating to the basis, and historical systematically assigned identifiers corresponding to the basis, a set of probable systematically assigned identifiers, or portions thereof, can be generated. For example, continuing with the example presented above in the context of step 125, if a received basis is an origination date, then a data source containing systematically assigned identifiers can be accessed in order to generate a set of probable systematically assigned identifiers having the same, similar, or proximate origination dates. As those skilled in the art will appreciate, generating a set of probable identifiers may employ other techniques, including a wide variety of statistical extrapolation methods. As with the steps within meta-step 105, steps within meta-step 120 may be performed in any order. The historical data source(s) consulted at optional steps 130 and 135 can include an electronic database, a print information source, a Internet webpage, a set of government records, or any other source of information that has been compiled or collected or is otherwise queryable.

Continuing with method 100, within meta-step 140, at step 145, the provided identifier received at step 110 is compared to a predicted set of statistically probable systematically assigned identifiers, discussed above in the context of meta-step 120, in order to determine a likelihood that the provided identifier is legitimate. Also, at step 150, a provided basis value is used as part of the comparison. The two sub-steps of meta-step 140 can test for at least two types of legitimacy of the provided identifier. For example, in some cases the legitimacy of the provided identifier can be attributed to the identifier itself. That is, the comparison focuses on whether the provided identifier has a legitimate format by containing the correct number and type of characters, whether the characters are arranged in a sequence that has been used in issued identifiers, and whether the identifier has actually been issued. In other examples, the legitimacy of the provided identifier can be attributed, in part, to the affiliation of the identifier with the identity of a particular person, entity, account, transaction, or piece of property. That is, even if the provided identifier has a legitimate format or is an issued identifier, it may not actually be associated with the entity purporting to be identified by it. In other words, even though the provided identifier itself is legitimate, its affiliation with a purported assignee may not be. Those skilled in the art will appreciate that other characteristics in addition to those described here may be used to verify legitimacy.

Given the immediately preceding context, at step 145 the provided identifier received at step 110 can be compared to a predicted a set of statistically probable systematically assigned identifiers. At this step, various aspects of the provided identifier is compared to set of identifiers, or portions thereof, predicted at meta-step 120. For example, as discussed above, the various characters and character combinations, location of certain characters, and format of the provided identifier can be compared to the constituents of the predicted set of identifiers in order to determine a likelihood of legitimacy. For example, use of uncommon characters or character combinations can decrease the likelihood that the provided identifier itself is legitimate. In other examples, a lack of a relationship, or a tenuous correlation, between a provided identifier and a provided value of a basis used as part of the system of assignment can also decrease a likelihood that the provided identifier is legitimately associated with the purported assignee. In yet other examples, likelihood of legitimacy can be based on the difference between the provided identifier and the predicted set of statistically probable systematically assigned identifiers, as well as, in part, the level of accuracy statistically expected from the predicted set.

Analogously, at step 150 within meta-step 140, a provided value of the at least one basis can be compared to an independent data source accessed at step 135 in order to assist the determination of a likelihood of legitimacy of the association between an entity and the provided identifier. For example, if a provider of an identifier purports to be a particular person, but provides a value of, for example, a birth date that does not match the birth date most likely to be associated with a particular person with that identifier, then the likelihood of legitimacy is accordingly reduced. Similarly, the provided value of a basis can be compared directly to the provided identifier in order to determine a likelihood of legitimacy. For example, if an identifier contains as part of its format elements of a specific basis, a provided value of that basis can be compared to the format elements of the identifier. For example, if the identifier format contains a representation of a birth date of an individual, but the birth date provided at step 115 is inconsistent with the representation contained by the identifier, the likelihood of legitimacy is reduced. Those skilled in the art will appreciate these examples are merely illustrative, and that many other types of bases can be used in the comparisons discussed at meta-step 140 in many different ways to validate legitimacy.

At step 155, a resulting likelihood of legitimacy can be communicated to a reviewer. While in some cases the likelihood can be communicated to a human reviewer using email, text message, fax, or otherwise displayed on a web page or other electronic communication medium, this is not necessarily the case. In other examples, a reviewer may be an electronic agent that receives the likelihood produced by method 100 at meta-step 140. As those skilled in the art will appreciate, a reviewer is a generic term referring to a person, machine, or system that can be responsive to the likelihood of legitimacy provided by meta-step 140.

FIG. 2 depicts an exemplary environment 200 that can be used to implement method 100 of FIG. 1. Environment 200 includes an identifier validating system 204 that is in operative communication with one or more querying machines 208. In this context, a "querying machine" is any machine, such as a laptop computer, desktop computer, workstation, tablet computer, Internet appliance, smartphone, personal multimedia device (e.g., an IPAD® device available from Apple, Inc., Cupertino, Calif.), etc. that allows a user (not shown) to initiate a query 212 as to the legitimacy of a provided identifier. System 200 is not limited to queries initiation by a user; indeed, the system may operate through submission or acquisition of information (whether a systematically assigned identifier, an identifier purported to be a systematically assigned identifier, or a value of a basis of systematic assignment) that is not directly submitted by a user or acquired from a user. In fact, querying machine 208 can include a "virtual machine" that is merely a programmed function within environment 200.

Typically, though not necessarily, the querying machine 208 that generates a particular query 212 will be the machine that receives an answer 216, for example, a likelihood of legitimacy, to that query from system 204. In the present example, each querying machine 208 is shown as being in operative communication with system 204 via cloud 220, which represents any one or more communications systems suitable for the particular instantiation of environment 200. For example, if a particular querying machine 208 is a desktop computer and system 204 is implemented in a web server, cloud 220 can represent, for example, the Internet and a local-area network (LAN) that the querying machine is connected to. As another example, if system 204 and each querying machine 208 are part of a site-specific enterprise system, cloud 220 can represent only a LAN. As a further example, if a particular querying machine 208 is a smartphone, cloud can represent the Internet, a cellular communications network, and any other communications system(s) needed to complete the communications path between that querying machine and system 204. Though not particularly illustrated, system 204 can be integrated into any of querying machines 208. Clearly, the possible environments for system 204 or a similar system incorporating various features of the present disclosure are myriad.

With the possible variations of environment 200 being so numerous, those skilled in the art will readily understand that the manners in which the user interfaces 228 for system 204 can be implemented are also diverse. For example, if system 204 is Web-based, user interface 228 at each querying machine 208 for query 212 and answer 216 can be Web-browser based. Alternatively, each querying machine 208 can execute a software application dedicated to providing a user interface 228 that is customized to system 204. However, if system 204 and querying machines 208 are parts of an on-site enterprise system, user interface 228 on each querying machine 208 can be a dedicated interface of the system. The same can be true in the case wherein system 204 is integrated into a querying machine 208.

Environment 200 also includes a number of data sources 232, each containing data that can be used to answer a query, such as query 212, depending on the content of that query. Each data source 232 can be virtually any source of data needed to satisfy a query, such as a database. Examples of databases that can be some or all of data sources 232 include, but are not limited to, databases corresponding to government records (e.g., social security records, IRS records, law enforcement and criminal justice system records, judicial records, etc.), financial records, financial transaction records, employer records, phone number and address databases, mailing databases, credit records and credit information databases, and many others. There is fundamentally no limitation on the type of database that can be a data source 232 useful to a particular instantiation of a system of the present disclosure, such as system 204 of FIG. 2. Data sources 232, like querying machines 208, can be local to system 204, local to any one or more of the querying machines, spread out over one or more networks, e.g., Internet or other wide-area network(s), LAN(s), wireless communications network(s), etc., and any combination thereof, as those skilled in the art will readily appreciate.

With the basics of method 100 and exemplary environment 200 having been described, attention is now turned to an illustrative implementation of method 100 (FIG. 1) using the environment and system 200. Referring now to FIG. 1, and also to FIG. 2, method 100 may begin at meta-step 105 at which system 204 receives a provided identifier and/or a value of at least one basis from the corresponding one of querying machines 208 as a query 212. As discussed above, query 212 need not be through a user-initiated act but instead can be initiated through a process initiated by system 200 upon being provided with an identifier or value at meta-step 105.

At meta-step 120, system 204, in response to being provided information at meta-step 105, predicts a set of statistically probable identifiers and/or a likelihood of legitimacy as answer 216 to query 212 using software 252. As those skilled in the art will readily understand, system 204 may access data sources 232 as part of the prediction steps through cloud 220, web server 224, or user interface 228, as described at optional steps 130 and/or 135.

Furthermore, software 252 may function through cloud 220, web server 224, or user interface 228 in order to compare an identifier provided at meta-step 105 with a set of statistically probable identifiers calculated at meta-step 120, as described above. Furthermore, as also explained above, software 252 may also operate to compare a provided value of at least one basis. Software may also function to communicate a resulting likelihood to a reviewer through, for example, a user interface 228.

As those skilled in the art can also readily understand, system 204 functionality can be readily instantiated in software 252 by skilled artisans. Such software 252 can be designed and configured for the particular configuration of environment 200. Exemplary instantiations of software 252 include a stand-alone application running on a server or a general-purpose computer, a set of software components running on differing machines, such as in the case of an application running on a server and an applet running on each querying machine, among others. Software 252 can also be designed and configured to be executed in a single- or multi-processor environment. The variations are diverse, and the general knowledge of a person of ordinary skill in the art would allow them to design and configure software 252 for any configuration of environment 200 without undue effort.

Social Security Number General Information

Turning now to the prediction and validation of a provided Social Security Number (SSN), as a specific exemplary application of the above-discussed methods and systems, the legitimacy of an SSN can be tested and verified using the examples of the present disclosure owing to the systematic method of assignment of the SSN. The structure of the SSN, and the method of assignment for each of the elements of the SSN are discussed below before proceeding to a discussion of exemplary methods and systems for verification.

An SSN, while containing nine digits, is composed of three numbers: The first three digits compose the Area Number (AN), the second two digits compose the Group Number (GN), and the last four digits compose the Serial Number (SN). Each of these three numbers is assigned to a person from a defined set of possible numbers according to a predictable pattern disclosed herein. Before discussing predictable pattern, and the analysis that it enables, a discussion of each of the numbers constituting an SSN follows.

An AN is assigned to a person based on the state from which the person is applying. Low-population states and certain U.S. possessions are allocated one AN each. Other, more populous states having more annual immigration and more births per year are each allocated a set of multiple ANs to accommodate the need in that state for a greater inventory of assignable SSNs. For example, New York state currently has 85 possible ANs. By contrast, less populous Oregon currently has five ANs. Within each state (that is for each set of ANs), GNs are assigned in a predictable, but nonconsecutive, order between 01 and 99. This order is as follows: 01, 03, 05, 07, 09, 10, 12, 14, . . . , (all remaining even numbers in order up to 98), 02, 04, 06, 08, 11, 13, 15, . . . , (all remaining odd numbers in order up to 99). Within each GN, SNs are assigned consecutively from 0001 to 9999.

Given the above structure, each of the three numbers forming an SSN advances in very predictable ways, as determined by an analysis of publicly available data in the Death Master File (DMF). The DMF records the birth date, assignment state, and SSN of every deceased person to have had an SSN. Based on an analysis of this data, it was determined that SNs change more frequently than ANs or GNs because they are assigned consecutively upon each assignment of an SSN. After assigning an SN of 9999, thereby exhausting all possible SNs for that particular AN/GN combination, the next AN in the series associated with that particular state is issued to the next SSN applicant, along with an SN of 0001. ANs advance in order from lowest number to highest number associated with the state. Upon reaching an SN of 9999 for the last AN associated with a particular state, the next GN according to the sequence described above is issued to the next SSN applicant along with an SN of 0001. This scheme is in contrast to the oft-held, and documented, belief that each of a state's ANs is assigned to a particular SN before advancing to the next SN.

The examples of the present disclosure directed to SSN validation take advantage of the increased correlation between the assigned SSN and the time and location of an individual's birth. This increased correlation is due in part to the federal "Enumeration at Birth" program that started being enacted in 1987, which permits an application for an SSN on behalf of an infant when the infant is born. The proximity between birth and SSN application means that there is a high degree of correlation between an SSN and the birth date and state. This correlation then facilitates the prediction of an unknown SSN based simply on an applicant's birth date and birth location, as disclosed herein. This correlation is most pronounced for states having comparatively small populations and low immigration rates, as illustrated by FIGS. 3A-3C.

Figure 3A:
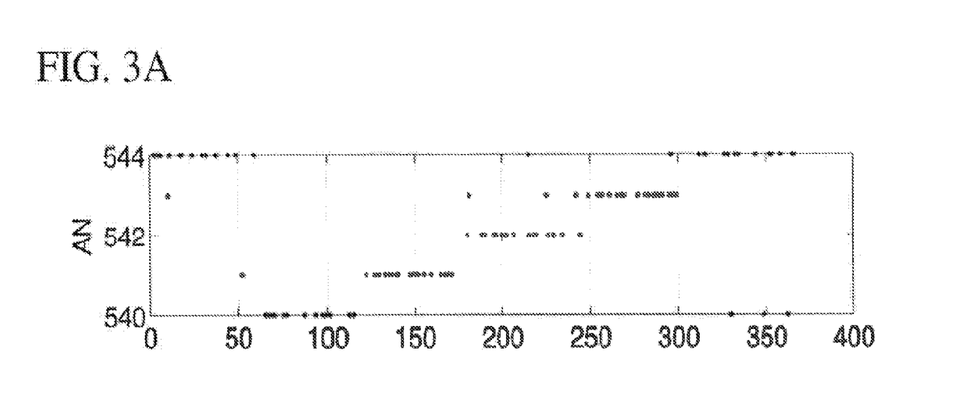
FIGS. 3A-3C illustrate exemplary systematic patterns of assigned Area Numbers, Group Numbers, and Serial Numbers within Social Security Numbers as a function of time for the state of Oregon.
Figure 3B:
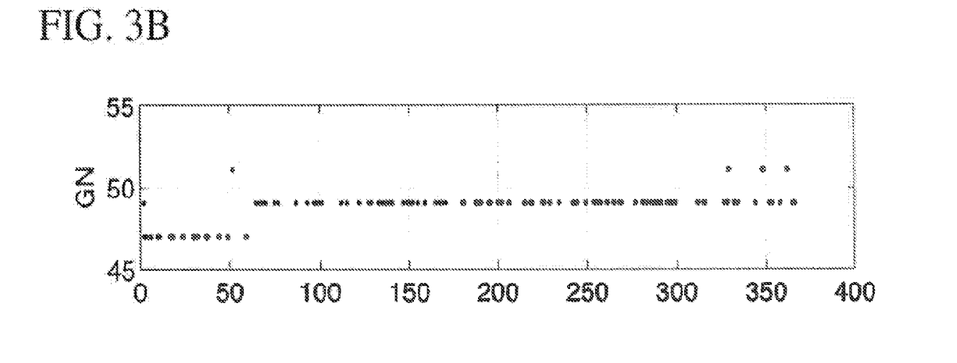
Figure 3C:
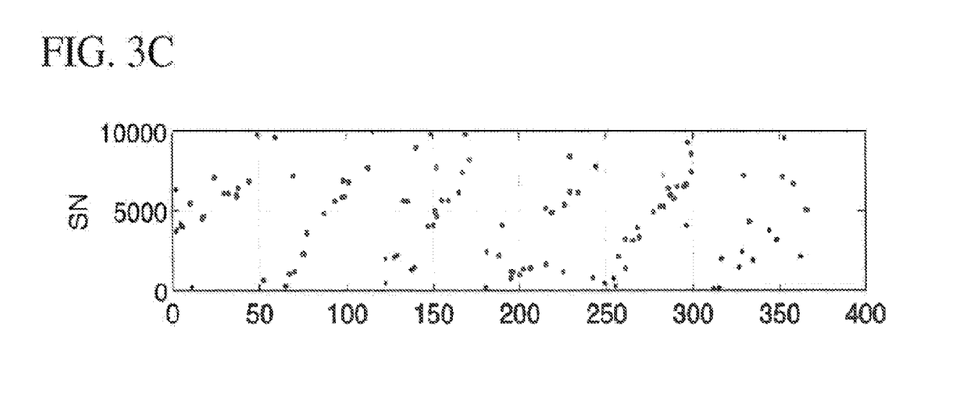

FIGS. 3A-3C illustrate the correlation discussed above by plotting separately AN, GN, and SN versus birth day (numbered consecutively from 1 to 365) for the state of Oregon for 1996. As can be seen, cyclical and chronological patterns in assignment are evident.

Prediction and Validation of Social Security Numbers

Figure 4:
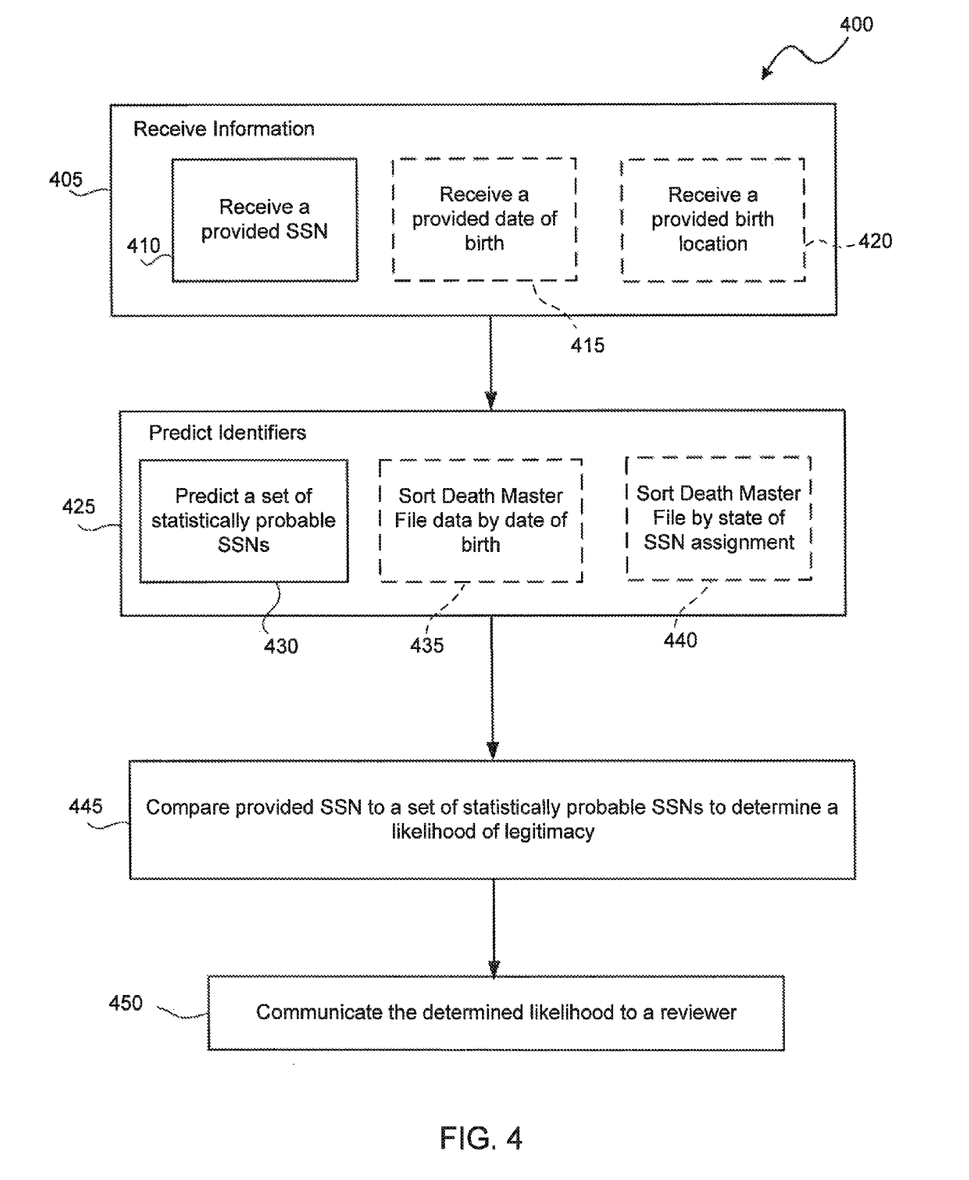
FIG. 4 illustrates a flow diagram depicting an exemplary embodiment of a method used to validate a provided Social Security Number.

FIG. 4 depicts a method 400 of verifying the legitimacy of a provided SSN, and of verifying the legitimacy of the association between the provided SSN and the purported assignee of the SSN. The verification of legitimacy is based, in part, on the foregoing observations of AN, GN, and SN advancement patterns as well as on other exemplary embodiments of methods and systems described above in the present disclosure. Within method 400, at meta-step 405, three types of information can be provided in any order to verify the legitimacies previously described. At step 410 an SSN is provided; at step 415 a date of birth of the purported assignee is provided; and at step 420 a birth location of the purported assignee is provided. In some examples, the birth location can be provided as a zip code; in other examples, it can be provided as a town or city and the state where the town or city is located; in yet other examples, it can be provided merely as a town or city without the state in which the town or city is located, and a probabilistic inference can be made regarding which is the most likely state where the town or city is located. The date of birth provided at step 415 and the birth location provided at step 420 can further enhance the predictive capabilities of method 400 as a result of the correlations described above. Also as described above, this information can be received by, for example, a human or electronic means.

At exemplary meta-step 425, three steps are conducted in to predict a set of statistically probable SSNs, or portions thereof. At step 430 a set of statistically probable SSNs is predicted. At step 435, DMF data is sorted by date of birth. At step 440, DMF data is sorted by state of SSN assignment. Those skilled in the art will appreciated that alternate orders of performing these steps are equally likely to produce a useable result. Is also noted that in some embodiments, the DMF data can be presorted so that method 400 does not need to include the corresponding steps, but rather would use the presorted data.

At step 430, based on the provided date of birth and/or provided birth location, a set of statistically probable SSNs, or portions thereof, is predicted. In one example, at optional step 435, DMF data for the state of birth implied by the AN of the provided SSN is segmented from the rest of the DMF and then sorted by date of birth. Then, using this segmented and sorted data, a test-window is centered on a date of birth provided at optional step 440 in order to begin production of a set of statistically probable SSNs, or portions thereof. The window, containing SSNs issued during the days contained within the window, can be one of at least two types. A first type, a variable window of time, e.g., days, can adjust the range of time sampled in order to capture the same number of births when analyzing more than one state with different birth rates (and therefore different SSN assignments per unit of time). Alternatively, a second type, a variable window of records, defines a constant range of time, e.g., days, around a date of interest thereby varying the number of births within the window.

The sorted DMF data can be further processed to enhance the reliability of the statistical predictions. For example, as explained above, the methods of the present disclosure directed to SSN validation presume a correlation between an individual's date of birth and the individual's SSN assignment. This correlation is due, in part, to the "Enumeration at Birth" program explained above. However, an SSN and a birth date may not be correlated in several examples, thereby complicating the verification of legitimacy. For example, an adult person receiving an SSN upon becoming a United States citizen would not have a birth date correlated with an SSN number. In other examples, parents may apply for an SSN on behalf of their child after moving from the child's birth state, thereby defying the correlation with both birth date and birth state. Furthermore, some SSNs and related dates are entered erroneously. These non-correlated data can be identified and removed in order to improve the accuracy of the AN/GN and the SN predictions, and therefore the accuracy of the provided SSN validation, using methods described in U.S. Provisional Patent Application Ser. No. 61/399,048, filed Jul. 6, 2001, and titled "Predicting and Validating Social Security Numbers from Public Data", which is incorporated by reference herein for its disclosure of such methods.

In either case, once the window is established around the provided date of birth and any DMF data cleansing performed, at step 430 a number of procedures can be performed in order to predict a set of statistically probable SSNs. For example, one such procedure identifies the AN/GN combination in the provided SSN. This procedure also generates a frequency of the various AN/GN combinations actually issued within the test-window of the segmented and sorted DMF data. Then, at step 445, a likelihood that the AN/GN combination is legitimate (i.e., whether or not the SSN is a valid number and whether or not the SSN was actually assigned to the purported assignee) can be produced by comparing the frequency of the actually issued AN/GN combinations to the provided AN/GN.

Another procedure that can be used at step 430 identifies the lowest SN and the highest SN issued on the provided date of birth using the predictive assumptions regarding AN, GN, and SN advancement described above, in combination with an approximated or estimated birth rate per day. Through use of the approximated or estimated birth rate per day, an estimate of the number of SNs assigned per day in the state can be calculated. Then, at step 445, the provided SN can then be compared to the identified highest and lowest SN assigned on the provided date of birth and the likelihood of legitimacy of the provided SN can thereby be determined.

In another procedure that can be used at step 430, all of the likely AN/GN combinations for a specific date, possibly a provided birth date, within a test-window applied to DMF data having been sorted by at least birth date or state, are calculated and ranked according to frequency until all likely AN/GN combinations are exhausted. Then, at step 445, a statistical measurement of the likelihood of legitimacy of the AN/GN combination of the provided SSN can be determined. For instance, the more distant is the provided AN/GN combination from the most frequent AN/GN combination or the most frequent AN/GN combinations in the window described above, the less likely the provided AN/GN is to be valid.

From the immediately preceding calculation, a set of probable SNs associated with the predicted AN/GN combinations, and possibly the provided date of birth and location of birth can be determined using a regression analysis. For example, an ordinary or a robust least squares regression can be used to fit a curve to the sorted DMF data. This curve, and its equation, can be used to measure how closely the SN issuance sequence is correlated to the provided date of birth accompanying the provided SSN. Using one of the test-window types previously described, but omitting the provided date of birth, the regression model $SN_i=\alpha+\beta_1 dd_{i,vw}+\beta_2 ANGN_{i,vw}+\epsilon_{i,vw}$ can be used to determine the linearity of SN assignment as a function of birth date. In this example "$SN_i$" is the SN assigned to individual i, born on day "dd" and whose record can be found within the variable window "vw" for a specific year and state. $ANGN_{i,vw}$ is a vector of dummies for the various ANGNs which can be found associated with the SSN records contained in that variable window. $\epsilon_{i,vw}$ is the regression error. $\alpha$, $\beta_1$, and $\beta_2$ are the regression parameters. Once those parameters have been estimated, they can be associated with the provided dd (the date of birth) and with the ANGN predicted based on the provided date of birth, in order to produce the predicted SN, which can then be compared to the provided SN to assess the legitimacy of the latter. As mentioned above in the context of FIG. 1, the more distant the provided SN is from the predicted SN, the less likely the provided SN is to be valid. In addition, the resulting $R^2$ provides a sense of how linear the relationship is between SN assignment and date of birth. Another result of this analysis is that the $R^2$ of the regression for the test-window provides a measure of probability that a legitimate SN would lie within a range of SN values, thereby performing step 445.

In a yet further procedure to determine a likelihood of legitimacy of a provided SSN that can be performed at step 430, a first test is run on the AN/GN combination of the of the provided SSN and for the provided date of birth. For example, if the provided date of birth is actually associated with a different predicted AN/GN combination, based on the foregoing sorting of DMF data, then the provided SSN is not legitimate. Assuming the provided SSN passes this test, then a polynomial model can be applied to determine the distribution of the provided AN/GN as a function of time. This can be performed by combining all AN/GN combinations used within a state in the provided birth year and centering a frequency distribution of the AN/GN combination around the provided birth date (e.g., the origin of the distribution). Based on this distribution, at step 445 the probability of the provided AN/GN actually being associated with the provided date of birth can be estimated.

In yet another procedure that can be performed at step 430, a likelihood of legitimacy can be determined for a provided SSN/date of birth combination. That is, whereas some examples can test whether a provided SSN has been issued, and therefore test whether the number itself is valid, this procedure tests whether the provider of the provided SSN is likely the legitimate assignee of the SSN. For example, using methods described above, a mean monthly AN/GN accuracy ratio, $r_{ANGN}$, and a mean monthly regression $R^2$, $r_{SN}$, are calculated for the AN/GN combinations and SNs of individuals born in the same month and the same state as the purported assignee. Next, a set of AN/GN combinations and SNs are predicted for the provided state of birth and provided date of birth. A likelihood of legitimacy score can then be calculated, among other ways, using two components: $1_1=\alpha_1 r_{ANGN}+\alpha_2 r_{SN}$; and $1_2=\alpha_3|A\tilde{N}/G\tilde{N}-AN/GN|+\alpha_4|S\tilde{N}-SN|$. In these equations, $\alpha_{1,2,3,4}$ are functional weights that can be selected appropriately depending on whether it is intended to give more importance in the validation process to the distance between predicted and provided AN/GN or SN, or the accuracy of the predicted ANs/GNs or SNs. Also in these equations, $r_{ANGN}$ and $r_{SN}$ are the mean monthly ANGN accuracy ratio and the mean monthly SN regression, respectively, of individuals born in the same month and state as the purported assignee using procedures described above. $A\tilde{N}/G\tilde{N}$ and $S\tilde{N}$ are the predicted AN/GN and SN values whereas AN/GN and SN are the values provided by the purported assignee.

Regarding the results of this procedure, the smaller $1_2$ and the larger $1_1$, the more likely that the provided SSN is legitimately assigned to the purported assignee. Similarly, the larger $1_2$ and the smaller $1_1$, the less likely that the assignment of the provided SSN is legitimate. In circumstances when $1_1$ is very small, the test may be inconclusive. The exact definition of "small" and "large" depend on the amount of false negatives (that is, the number of incorrect SSNs assumed to be correct) and false positives (correct SSNs assumed to be incorrect) that can be accepted.

Furthermore, the foregoing analyses notwithstanding, the comparison performed at step 430 can be accomplished using any number of algorithms and sub-methods, particularly given the patterns of SSN assignment disclosed above. For example, at step 445, without producing a set of statistically probable methods is predicted, the provided SSN can be tested for legitimacy by using methods disclosed above and checking whether each of the provided AN, GN, and SN of the provided SSN is valid. Specifically, the AN can be checked against known issued ANs, the AN and GN combination can be tested to confirm that the combination has been issued, and the SN is similarly valid e.g., is not 0000 (which is not issued by the Social Security Administration for any SSN).

At step 450, the likelihood of legitimacy can be communicated to a reviewer, as explained in the context of method 100.

Figure 5:
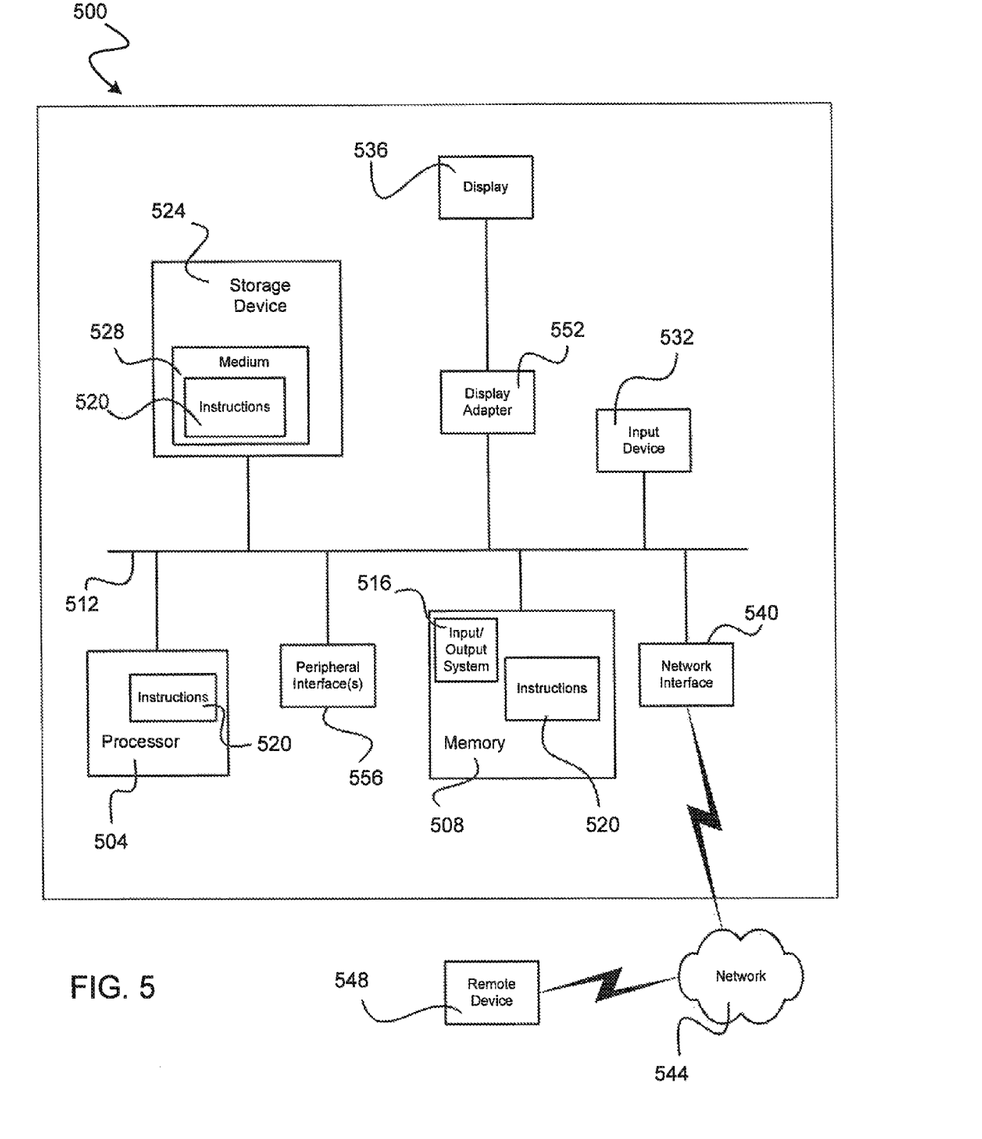
FIG. 5 is a high-level schematic diagram of an exemplary software-driven machine capable of implementing methods of the present invention.

FIG. 5 shows a diagrammatic representation of one embodiment of a computer in the exemplary form of a computer system 500 that contains a set of instructions for implementing any one or more of the aspects and/or methodologies of the present disclosure, including implementing software 252 depicted in FIG. 2 and the software for implementing method 400 of FIG. 4. As an example, computer system 500 can be used as Web server 224 of FIG. 4. It is contemplated that multiple computing devices may be utilized to implement a specially configured set of instructions for causing the device to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine readable media) including, but not limited to, a random access memory component (e.g., a static RAM "SRAM", a dynamic RAM "DRAM", etc.), a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable storage media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive for reading from and/or writing to a hard disk, a magnetic disk drive for reading from and/or writing to a removable magnetic disk, an optical disk drive for reading from and/or writing to an optical medium (e.g., a CD, a DVD, etc.), a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable storage medium 528 may provide nonvolatile and/or volatile storage of machine-readable instructions, data structures, program modules, and/or other data for computer system 500. In one example, software 520 may reside, completely or partially, within machine-readable storage medium 528. In another example, software 520 may reside, completely or partially, within processor 504. It is noted that the term "machine-readable storage medium" does not include signals present on one or more carrier waves.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540 may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. In addition to a display device, a computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

Further alternative exemplary embodiments of the present invention are described in the paragraphs below.

In one example, a method of validating a provided identifier purported to be a systematically assigned identifier and purported to correspond to an entity, the systematically assigned identifier has at least one basis of systematic assignment, the method comprises receiving the provided identifier; receiving a value of the at least one basis purportedly associated with the provided identifier; predicting a set of statistically probable systematically assigned identifiers as a function of the value; comparing the provided identifier to the set of statistically probable systematically assigned identifiers so as to determine a likelihood that the provided identifier is legitimate; and communicating the likelihood resulting from the comparison to a reviewer. Such an exemplary embodiment may also include one or more of the following features:

The at least one basis includes a geographic region corresponding to the provider of the identifier.

The predicting further includes reference to a database including a plurality of values of at least one basis.

The comparing includes evaluating a distance between the provided identifier and the set of statistically probable systematically assigned identifiers.

Using a measure of accuracy of the set of statistically probable systematically assigned identifiers.

The comparing includes determining a level of accuracy of the set of statistically probable systematically assigned identifiers.

The at least one basis includes a geographic region.
The at least one basis includes an issue date.
The at least one basis includes a birth date.
The at least one basis includes an application date.
The predicting includes performing a linear regression analysis.

The predicting includes statistically analyzing assignment patterns of the systematically assigned identifier.

The statistically analyzing includes determining assignment patterns of the systematically assigned identifier.

The assignment patterns include identifying a plurality of commonly assigned identifiers.

The predicting includes comparing the value of the at least one basis of the provided identifier to publicly available information corresponding to the entity.

The predicting includes comparing the at least one basis of the provided identifier to non-publicly available information associated with the entity.

The non-publicly available information includes credit history information corresponding to the entity.

In another example, a machine-readable storage medium containing machine-executable instructions for performing a method of validating a provided identifier purported to be a systematically assigned identifier and purported to correspond to an entity, the systematically assigned identifier has at least one basis of systematic assignment, the machine executable instructions comprise a first set of machine-executable instructions for receiving the provided identifier; a second set of machine-executable instructions for receiving a value of the at least one basis purportedly associated with the provided identifier; a third set of machine-executable instructions for predicting a set of statistically probable systematically assigned identifiers as a function of the value; a fourth set of machine-executable instructions for comparing the provided identifier to the set of statistically probable systematically assigned identifiers so as to determine a likelihood that the provided identifier is legitimate; and a fifth set of machine-executable instructions for communicating the likelihood resulting from the comparison to a reviewer. Such an exemplary embodiment may also include one or more of the following features:

The third set of machine-executable instructions includes statistically analyzing assignment patterns of the systematically assigned identifier.

The statistically analyzing includes determining assignment patterns of the systematically assigned identifier.

The assignment patterns include identifying a plurality of commonly assigned identifiers.

The fourth set of machine-executable instructions includes evaluating a distance between the provided identifier and the set of statistically probable systematically assigned identifiers.

The fourth set of machine-executable instructions includes determining a level of accuracy of the set of statistically probable systematically assigned identifiers.

The at least one basis includes a geographic region corresponding to the provider of the identifier.

The at least one basis includes a geographic region.

The at least one basis includes an issue date.

The at least one basis includes a birth date.

The at least one basis includes an application date.

The third set of machine-executable instructions includes machine-executable instructions for performing a linear regression analysis.

The third set of machine-executable instructions includes a statistical analysis of assignment patterns of the systematically assigned identifier.

The fourth set of machine-executable instructions includes machine-executable instructions for comparing the value of the at least one basis of the provided identifier to publicly available information corresponding to the entity.

The fourth set of machine-executable instructions includes machine-executable instructions for comparing the at least one basis of the provided identifier to non-publicly available information associated with the entity.

The non-publicly available information includes credit history information corresponding to the entity.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A machine-readable storage medium containing machine-executable instructions for performing a method of validating a provided Social Security Number having a Group Number purported to be associated with a person, the machine-executable instructions comprising:

a first set of machine-executable instructions for receiving the provided Social Security Number;

a second set of machine-executable instructions for predicting a set of statistically probable Social Security Numbers, wherein said second set of machine-executable instructions includes:

machine-executable instructions for estimating an average birth rate for a state; and machine-executable instructions for using the average birth rate to estimate a frequency at which the Group Number changes;

a third set of machine-executable instructions for comparing the provided Social Security Number to the set of statistically probable Social Security Numbers so as to determine a likelihood that the provided Social Security Number is legitimate; and a fourth set of machine-executable instructions for communicating the likelihood to a reviewer.

2. A machine-readable storage medium according to claim 1, wherein said third set of machine-executable instructions includes statistically analyzing assignment patterns of the Social Security Number, said statistically analyzing including determining assignment patterns of the Social Security Number.

3. A machine-readable storage medium according to claim 2, wherein said assignment patterns include identifying a plurality of commonly assigned Social Security Numbers.

4. A machine-readable storage medium according to claim 1, wherein said third set of machine-executable instructions includes evaluating a distance between the provided Social Security Number and the set of statistically probable systematically assigned Social Security Numbers.

5. A machine-readable storage medium according to claim 4, wherein said third set of machine-executable instructions includes using a measure of accuracy of the set of statistically probable systematically assigned Social Security Numbers.

6. A machine-readable storage medium according to claim 1, wherein said third set of machine-executable instructions includes determining a level of accuracy of the set of statistically probable systematically assigned Social Security Numbers.

7. A machine-readable storage medium according to claim 1, further comprising machine-executable instructions for receiving a provided date of birth purported to be the date of birth of the person purported to be associated with the provided Social Security Number.

8. A machine-readable storage medium according to claim 7, wherein said second set of machine-executable instructions further includes machine-executable instructions for using Death Master File data.

9. A machine-readable storage medium according to claim 8, further comprising machine-executable instructions for sorting the Death Master File data by date of birth so as to facilitate said predicting by viewing Social Security Numbers proximate to the provided date of birth.

10. A machine-readable storage medium according to claim 9, further comprising machine-executable instructions for removing outlier Social Security Numbers from sorted Death Master File data deviating substantially from a linear correlation between Social Security Number and date of birth.

11. A machine-readable storage medium according to claim 10, wherein said machine-executable instructions for removing includes:

machine-executable instructions for selecting a set of Death Master File records associated with an Area Number/Group Number combination, each record within the set having a date of birth and at least one Serial Number associated with the date of birth;

machine-executable instructions for performing a regression analysis on the set, wherein the regression analysis includes an independent variable and a dependent variable, and further includes using the date of birth as the dependent variable and the at least one Serial Number as the independent variable;

machine-executable instructions for calculating a regression residual for the date of birth;

machine-executable instructions for computing an inter-quartile range for the date of birth using the regression residual; and machine-executable instructions for using the inter-quartile range to identify and eliminate outlier dates of birth associated with the Area Number/Group Number combination.

12. A machine-readable storage medium according to claim 7, wherein said second set of machine-executable instructions further includes machine-executable instructions for using the provided date of birth to limit the set of statistically probable Social Security Numbers to those proximate to the provided date of birth.

13. A machine-readable storage medium according to claim 1, wherein the Social Security Number has an Area Number and said second set of machine-executable instructions further includes using a birth location to predict the Area Number.

14. A machine-readable storage medium according to claim 13, wherein said second set of machine-executable instructions further includes using a birth date to predict the Area Number.

15. A machine-readable storage medium according to claim 14, wherein said third set of machine-executable instructions includes machine-executable instructions for comparing a predicted Area Number/Group Number combination for a provided birth date for all of the states.

16. A machine-readable storage medium according to claim 1, wherein said second set of machine-executable instructions further includes machine-executable instructions for analyzing Area Numbers, Group Numbers and dates of birth contained in a Death Master File, and machine-executable instructions for analyzing Serial Numbers associated with the birth dates, thereby determining a correlation between the birth dates and the Serial Numbers.

17. A machine-readable storage medium according to claim 16, wherein said second set of machine-executable instructions further includes machine-executable instructions for implementing a regression model.

18. A machine-readable storage medium according to claim 17, wherein the regression model is $$SN_i = \alpha + \beta_1 dd_{i,vw} + \beta_2 ANGN_{i,vw} + \epsilon_{i,vw}$$

wherein:
  $SN_i$ is a Serial Number assigned to individual i;
  $\alpha$ is a first regression parameter;
  $\beta_1$ is a second regression parameter;
  $dd_{i,vw}$ is individual i's birth date whose record can be found in a variable window vw for a specific state and a specific year;
  $\beta_2$ is a third regression parameter;
  $ANGN_{i,vw}$ is a vector of dummies for ANGNs that can be found associated with Social Security Number records contained in the variable window; and
  $\epsilon_{i,vw}$ is a regression error.

19. A machine-readable storage medium according to claim 1, further comprising machine-executable instructions for receiving a provided location of birth purported to be a location of birth of the person purported to be associated with the provided Social Security Number, said second set of machine-executable instructions including machine-executable instructions for using the provided location of birth to limit the set of statistically probable Social Security Numbers to those affiliated with the location of birth through an Area Number.

20. A machine-readable storage medium according to claim 19, wherein said second set of machine-executable instructions further includes machine-executable instructions for basing the statistically probable Social Security Numbers on a set of common Area Numbers and a set of common Group Numbers occurring in a Death Master File within a variable window of days approximately centered around the provided Social Security Number.

21. A machine-readable storage medium according to claim 19, wherein said second set of machine-executable instructions further includes machine-executable instructions for basing the statistically probable Social Security Numbers on a set of most common Area Numbers and a set of most common Group Numbers occurring in a Death Master File within a variable window of Social Security Numbers approximately centered around the provided Social Security Number.

22. A machine-readable storage medium according to claim 21, wherein the variable window is determined using a birth rate of a U.S. state.

23. A machine-readable storage medium according to claim 1, further comprising machine-executable instructions for confirming a provided Area Number of the provided Social Security Number has been issued by the Social Security Administration.

24. A machine-readable storage medium according to claim 23, further comprising machine-executable instructions for confirming that a provided Area Number of the provided Social Security Number is associated with a state corresponding to a provided state of birth purported to be associated with the provided Social Security Number.

25. A machine-readable storage medium according to claim 1, further comprising machine-executable instructions for confirming a provided Group Number of the provided Social Security Number has been issued by the Social Security Administration.

26. A machine-readable storage medium according to claim 1, wherein said second set of machine-executable instructions further includes:
  machine-executable instructions for receiving a provided birth location and a provided date of birth purported to be associated with the provided Social Security Number;
  machine-executable instructions for sorting Death Master File records by state;
  machine-executable instructions for ordering the sorted records by date of birth; and
  machine-executable instructions for identifying a window of ordered and sorted Death Master File records centered on the provided date of birth for the provided birth location.

27. A machine-readable storage medium according to claim 26, wherein said second set of machine-executable instructions further includes machine-executable instructions for determining at least one Area Number and at least one Group Number associated with the window of ordered and sorted Death Master File records.

28. A machine-readable storage medium according to claim 26, wherein said second set of machine-executable instructions further includes machine-executable instructions for determining a highest Serial Number and a lowest Serial Number issued on the provided date of birth for the provided birth location.

29. A machine-readable storage medium according to claim 26, wherein said machine-executable instructions for identifying a window includes machine-executable instructions for using a variable number of days window.

30. A machine-readable storage medium according to claim 26, wherein said machine-executable instructions for identifying a window includes machine-executable instructions for using a fixed number of records window.

31. A machine-readable storage medium according to claim 26, further comprising machine-executable instructions for predicting a set of likely Area Numbers and Group Numbers at a given statistical confidence interval for the provided birth location on the provided date of birth.

32. A machine-readable storage medium according to claim 31, wherein the set includes all Area Number/Group Number combinations using a set of Area Numbers and a set of Group Numbers published for the provided birth location and the provided date of birth.

33. A machine-readable storage medium according to claim 26, further comprising machine-executable instructions for predicting a set of likely Serial Numbers at a given statistical confidence interval for the provided birth location on the provided date of birth.

34. A machine-readable storage medium according to claim 1, further comprising a set of machine-executable instructions for measuring the accuracy of the set of statistically probable Social Security Numbers using a legitimacy score.

35. A machine-readable storage medium according to claim 34, wherein the legitimacy score includes a parameter $1_1$ and a parameter $1_2$, further wherein:

$1_1$ is equal to $\alpha_1 r_{ANGN} + \alpha_2 r_{SN}$;

$1_2$ is equal to $\alpha_3 |AN/GN - A\check{n}/G\check{N}| + \alpha_4 |S\check{N} - SN|$;

$\alpha_{1,2,3,4}$ are functional weights;

$r_{ANGN}$ is a mean monthly Area Number and Group Number accuracy ratio of individuals born in the same month and state as a purported assignee;

$r_{SN}$ is a mean monthly Serial Number regression of individuals born in the same month and state as the purported assignee;

$A\check{N}/G\check{N}$ are predicted Area Number and Group Number values;

$S\check{N}$ is a predicted Serial Number values;

AN/GN are Area Number and Group Number values provided by the purported assignee; and SN are Serial Number values provided by the purported assignee.

36. A machine-readable storage medium containing machine-executable instructions for performing a method of validating a provided Social Security Number purported to be associated with a person, the machine-executable instructions comprising:

a first set of machine-executable instructions for receiving the provided Social Security Number;

a second set of machine-executable instructions for predicting a set of statistically probable Social Security Numbers, said second set including machine-executable instructions for using Death Master File data;

a third set of machine-executable instructions for comparing the provided Social Security Number to the set of statistically probable Social Security Numbers so as to determine a likelihood that the provided Social Security Number is legitimate;

a fourth set of machine-executable instructions for communicating the likelihood to a reviewer;

machine-executable instructions for receiving a provided date of birth purported to be the date of birth of the person purported to be associated with the provided Social Security Number; and machine-executable instructions for sorting the Death Master File data by date of birth so as to facilitate said predicting by viewing Social Security Numbers proximate to the provided date of birth.

37. A machine-readable storage medium according to claim 36, further comprising machine-executable instructions for removing outlier Social Security Numbers from sorted Death Master File data deviating substantially from a linear correlation between Social Security Number and date of birth.

38. A machine-readable storage medium according to claim 37, wherein said machine-executable instructions for removing includes:

machine-executable instructions for selecting a set of Death Master File records associated with an Area Number/Group Number combination, each record within the set having a date of birth and at least one Serial Number associated with the date of birth;

machine-executable instructions for performing a regression analysis on the set, wherein the regression analysis includes an independent variable and a dependent variable, and further includes using the date of birth as the dependent variable and the at least one Serial Number as the independent variable;

machine-executable instructions for calculating a regression residual for the date of birth;

machine-executable instructions for computing an inter-quartile range for the date of birth using the regression residual; and machine-executable instructions for using the inter-quartile range to identify and eliminate outlier dates of birth associated with the Area Number/Group Number combination.

39. A machine-readable storage medium according to claim 36, wherein said second set of machine-executable instructions includes machine-executable instructions for analyzing Area Numbers, Group Numbers and dates of birth contained in a Death Master File, and machine-executable instructions for analyzing Serial Numbers associated with the birth dates, thereby determining a correlation between the birth dates and the Serial Numbers.

40. A machine-readable storage medium according to claim 39, wherein said second set of machine-executable instructions includes machine-executable instructions for implementing a regression model.

41. A machine-readable storage medium according to claim 40, wherein the regression model is $$SN_i = \alpha + \beta_1 dd_{i,vw} + \beta_2 ANGN_{i,vw} + \epsilon_{i,vw}$$

wherein:

$SN_i$ is a Serial Number assigned to individual i;

$\alpha$ is a first regression parameter;

$\beta_1$ is a second regression parameter;

$dd_{i,vw}$ is individual i's birth date whose record can be found in a variable window vw for a specific state and a specific year;

$\beta_2$ is a third regression parameter;

$ANGN_{i,vw}$ is a vector of dummies for ANGNs that can be found associated with Social Security Number records contained in the variable window; and $\epsilon_{i,vw}$ is a regression error.

42. A machine-readable storage medium according to claim 36, further comprising machine-executable instructions for receiving a provided location of birth purported to be a location of birth of the person purported to be associated with the provided Social Security Number; wherein said second set of machine-executable instructions further comprises machine-executable instructions for using the provided location of birth to limit the set of statistically probable Social Security Numbers to those affiliated with the location of birth through an Area Number.

43. A machine-readable storage medium according to claim 42, wherein said second set of machine-executable instructions further includes machine-executable instructions for basing the statistically probable Social Security Numbers on a set of common Area Numbers and a set of common Group Numbers occurring in a Death Master File within a variable window of days approximately centered around the provided Social Security Number.

44. A machine-readable storage medium according to claim 36, wherein said second set of machine-executable instructions further includes machine-executable instructions for basing the statistically probable Social Security Numbers on a set of common Area Numbers and a set of common Group Numbers occurring in a Death Master File within a variable window of days approximately centered around the provided Social Security Number.

45. A machine-readable storage medium according to claim 36, wherein said second set of machine-executable instructions further includes machine-executable instructions for basing the statistically probable Social Security Numbers on a set of most common Area Numbers and a set of most common Group Numbers occurring in the Death Master File within a variable window of Social Security Numbers approximately centered around the provided Social Security Number.

46. A machine-readable storage medium according to claim 36, further comprising a set of machine-executable instructions for measuring the accuracy of the set of statistically probable Social Security Numbers using a legitimacy score, wherein the legitimacy score includes a parameter $1_1$ and a parameter $1_2$, further wherein:

$1_1$ is equal to $\alpha_1 r_{ANGN} + \alpha_2 r_{SN}$;
$1_2$ is equal to $\alpha_3 |A\check{N}/G\check{N} - AN/GN| + \alpha_4 |S\check{N} - SN|$;
$\alpha_{1,2,3,4}$ are functional weights;
$r_{ANGN}$ is a mean monthly Area Number and Group Number accuracy ratio of individuals born in the same month and state as a purported assignee;
$r_{SN}$ is a mean monthly Serial Number regression of individuals born in the same month and state as the purported assignee;
$A\check{N}/G\check{N}$ are predicted Area Number and Group Number values;
$S\check{N}$ is a predicted Serial Number values;
AN/GN are Area Number and Group Number values provided by the purported assignee; and
SN are Serial Number values provided by the purported assignee.

47. A machine-readable storage medium containing machine-executable instructions for performing a method of validating a provided Social Security Number purported to be associated with a person, the machine-executable instructions comprising:
a first set of machine-executable instructions for receiving the provided Social Security Number;
a second set of machine-executable instructions for predicting a set of statistically probable Social Security Numbers, said second set of machine-executable instructions including:
machine-executable instructions for analyzing Area Numbers, Group Numbers and dates of birth contained in a Death Master File; and
machine-executable instructions for analyzing Serial Numbers associated with the birth dates, thereby determining a correlation between the birth dates and the Serial Numbers;
a third set of machine-executable instructions for comparing the provided Social Security Number to the set of statistically probable Social Security Numbers so as to determine a likelihood that the provided Social Security Number is legitimate; and
a fourth set of machine-executable instructions for communicating the likelihood to a reviewer.

48. A machine-readable storage medium according to claim 47, wherein said second set of machine-executable instructions includes machine-executable instructions for implementing a regression model.

49. A machine-readable storage medium according to claim 48, wherein the regression model is $$SN_i = \alpha + \beta_1 dd_{i,vw} + \beta_2 ANGN_{i,vw} + \epsilon_{i,vw}$$

wherein:
$SN_i$ is a Serial Number assigned to individual i;
$\alpha$ is a first regression parameter;
$\beta_1$ is a second regression parameter;
$dd_{i,vw}$ is individual i's birth date whose record can be found in a variable window vw for a specific state and a specific year;
$\beta_2$ is a third regression parameter;
$ANGN_{i,vw}$ is a vector of dummies for ANGNs that can be found associated with Social Security Number records contained in the variable window; and
$\epsilon_{i,vw}$ is a regression error.

50. A machine-readable storage medium according to claim 47, wherein said second set of machine-executable instructions further includes machine-executable instructions for basing the statistically probable Social Security Numbers on a set of common Area Numbers and a set of common Group Numbers occurring in the Death Master File within a variable window of days approximately centered around the provided Social Security Number.

51. A machine-readable storage medium according to claim 47, wherein said second set of machine-executable instructions further includes machine-executable instructions for basing the statistically probable Social Security Numbers on a set of most common Area Numbers and a set of most common Group Numbers occurring in the Death Master File within a variable window of Social Security Numbers approximately centered around the provided Social Security Number.

52. A machine-readable storage medium according to claim 47, wherein said second set of machine-executable instructions further includes:
machine-executable instructions for receiving a provided birth location and a provided date of birth purported to be associated with the provided Social Security Number;
machine-executable instructions for sorting Death Master File records by state;
machine-executable instructions for ordering the sorted records by date of birth; and machine-executable instructions for identifying a window of ordered and sorted Death Master File records centered on the provided date of birth for the provided birth location.

53. A machine-readable storage medium according to claim 47, further comprising a set of machine-executable instructions for measuring the accuracy of the set of statistically probable Social Security Numbers using a legitimacy score, wherein the legitimacy score includes a parameter $1_1$ and a parameter $1_2$, further wherein:

$1_1$ is equal to $\alpha_1 r_{ANGN} + \alpha_2 r_{SN}$;
$1_2$ is equal to $\alpha_3 |A\check{N}/G\check{N} - AN/GN| + \alpha_4 |S\check{N} - SN|$;
$\alpha_{1,2,3,4}$ are functional weights;
$r_{ANGN}$ is a mean monthly Area Number and Group Number accuracy ratio of individuals born in the same month and state as a purported assignee;
$r_{SN}$ is a mean monthly Serial Number regression of individuals born in the same month and state as the purported assignee;
$A\check{N}/G\check{N}$ are predicted Area Number and Group Number values;
$S\check{N}$ is a predicted Serial Number values;
AN/GN are Area Number and Group Number values provided by the purported assignee; and
SN are Serial Number values provided by the purported assignee.

54. A machine-readable storage medium containing machine-executable instructions for performing a method of validating a provided Social Security Number purported to be associated with a person, the machine-executable instructions comprising:

a first set of machine-executable instructions for receiving the provided Social Security Number and a provided location of birth purported to be a location of birth of the person purported to be associated with the provided Social Security Number;

a second set of machine-executable instructions for predicting a set of statistically probable Social Security Numbers, said second set of machine-executable instructions including:
  instructions for using the provided location of birth to limit the set of statistically probable Social Security Numbers to those affiliated with the location of birth through an Area Number; and
  instructions for basing the statistically probable Social Security Numbers on a set of common Area Numbers and a set of common Group Numbers occurring in a Death Master File within a variable window of days approximately centered around the provided Social Security Number;

a third set of machine-executable instructions for comparing the provided Social Security Number to the set of statistically probable Social Security Numbers so as to determine a likelihood that the provided Social Security Number is legitimate; and a fourth set of machine-executable instructions for communicating the likelihood to a reviewer.

55. A machine-readable storage medium according to claim 54, further comprising a set of machine-executable instructions for measuring the accuracy of the set of statistically probable Social Security Numbers using a legitimacy score, wherein the legitimacy score includes a parameter $1_1$ and a parameter $1_2$, further wherein:

$1_1$ is equal to $\alpha_1 r_{ANGN} + \alpha_2 r_{SN}$;
$1_2$ is equal to $\alpha_3 |A\check{N}/G\check{N} - AN/GN| + \alpha_4 |S\check{N} - SN|$;
$\alpha_{1,2,3,4}$ are functional weights;
$r_{ANGN}$ is a mean monthly Area Number and Group Number accuracy ratio of individuals born in the same month and state as a purported assignee;
$r_{SN}$ is a mean monthly Serial Number regression of individuals born in the same month and state as the purported assignee;
$A\check{N}/G\check{N}$ are predicted Area Number and Group Number values;
$S\check{N}$ is a predicted Serial Number values;
AN/GN are Area Number and Group Number values provided by the purported assignee; and
SN are Serial Number values provided by the purported assignee.

56. A machine-readable storage medium containing machine-executable instructions for performing a method of validating a provided Social Security Number purported to be associated with a person, the machine-executable instructions comprising:

a first set of machine-executable instructions for receiving the provided Social Security Number and a provided location of birth purported to be a location of birth of the person purported to be associated with the provided Social Security Number;

a second set of machine-executable instructions for predicting a set of statistically probable Social Security Numbers, said second set of machine-executable instructions including:
  instructions for using the provided location of birth to limit the set of statistically probable Social Security Numbers to those affiliated with the location of birth through an Area Number; and
  instructions for basing the statistically probable Social Security Numbers on a set of most common Area Numbers and a set of most common Group Numbers occurring in a Death Master File within a variable window of Social Security Numbers approximately centered around the provided Social Security Number;

a third set of machine-executable instructions for comparing the provided Social Security Number to the set of statistically probable Social Security Numbers so as to determine a likelihood that the provided Social Security Number is legitimate; and a fourth set of machine-executable instructions for communicating the likelihood to a reviewer.

57. A machine-readable storage medium according to claim 56, wherein the variable window is determined using a birth rate of a U.S. state.

58. A machine-readable storage medium according to claim 56, further comprising a set of machine-executable instructions for measuring the accuracy of the set of statistically probable Social Security Numbers using a legitimacy score, wherein the legitimacy score includes a parameter $1_1$ and a parameter $1_2$, further wherein:

$1_1$ is equal to $\alpha_1 r_{ANGN} + \alpha_2 r_{SN}$;
$1_2$ is equal to $\alpha_3 |A\check{N}/G\check{N} - AN/GN| + \alpha_4 |S\check{N} - SN|$;
$\alpha_{1,2,3,4}$ are functional weights;
$r_{ANGN}$ is a mean monthly Area Number and Group Number accuracy ratio of individuals born in the same month and state as a purported assignee;
$r_{SN}$ is a mean monthly Serial Number regression of individuals born in the same month and state as the purported assignee;
$A\check{N}/G\check{N}$ are predicted Area Number and Group Number values;
$S\check{N}$ is a predicted Serial Number values;

AN/GN are Area Number and Group Number values provided by the purported assignee; and SN are Serial Number values provided by the purported assignee.

59. A machine-readable storage medium containing machine-executable instructions for performing a method of validating a provided Social Security Number purported to be associated with a person, the machine-executable instructions comprising:
- a first set of machine-executable instructions for receiving the provided Social Security Number;
- a second set of machine-executable instructions for predicting a set of statistically probable Social Security Numbers, said second set of machine-executable instructions including:
  - machine-executable instructions for receiving a provided birth location and a provided date of birth purported to be associated with the provided Social Security Number;
  - machine-executable instructions for sorting Death Master File records by state;
  - machine-executable instructions for ordering the sorted records by date of birth; and
  - machine-executable instructions for identifying a window of ordered and sorted Death Master File records centered on the provided date of birth for the provided birth location;
- a third set of machine-executable instructions for comparing the provided Social Security Number to the set of statistically probable Social Security Numbers so as to determine a likelihood that the provided Social Security Number is legitimate; and
- a fourth set of machine-executable instructions for communicating the likelihood to a reviewer.

60. A machine-readable storage medium according to claim 59, wherein said second set of machine-executable instructions includes machine-executable instructions for determining at least one Area Number and at least one Group Number associated with the window of ordered and sorted Death Master File records.

61. A machine-readable storage medium according to claim 59, wherein said second set of machine-executable instructions includes machine-executable instructions for determining a highest Serial Number and a lowest Serial Number issued on the provided date of birth for the provided birth location.

62. A machine-readable storage medium according to claim 59, wherein said machine-executable instructions for identifying a window includes machine-executable instructions for using a variable number of days window.

63. A machine-readable storage medium according to claim 59, wherein said machine-executable instructions for identifying a window includes machine-executable instructions for using a fixed number of records window.

64. A machine-readable storage medium according to claim 59, further comprising machine-executable instructions for predicting a set of likely Area Numbers and Group Numbers at a given statistical confidence interval for the provided birth location on the provided date of birth.

65. A machine-readable storage medium according to claim 64, wherein the set includes all Area Number/Group Number combinations using a set of Area Numbers and a set of Group Numbers published for the provided birth location and the provided date of birth.

66. A machine-readable storage medium according to claim 59, further comprising machine-executable instructions for predicting a set of likely Serial Numbers at a given statistical confidence interval for the provided birth location on the provided date of birth.

67. A machine-readable storage medium according to claim 59, further comprising a set of machine-executable instructions for measuring the accuracy of the set of statistically probable Social Security Numbers using a legitimacy score, wherein the legitimacy score includes a parameter $1_1$ and a parameter $1_2$, further wherein:
- $1_1$ is equal to $\alpha_1 r_{ANGN} + \alpha_2 r_{SN}$;
- $1_2$ is equal to $\alpha_3 |A\check{N}/G\check{N} - AN/GN| + \alpha_4 |S\check{N} - SN|$;
- $\alpha_{1,2,3,4}$ are functional weights;
- $r_{ANGN}$ is a mean monthly Area Number and Group Number accuracy ratio of individuals born in the same month and state as a purported assignee;
- $r_{SN}$ is a mean monthly Serial Number regression of individuals born in the same month and state as the purported assignee;
- $A\check{N}/G\check{N}$ are predicted Area Number and Group Number values;
- $S\check{N}$ is a predicted Serial Number values;
- AN/GN are Area Number and Group Number values provided by the purported assignee; and
- SN are Serial Number values provided by the purported assignee.

68. A machine-readable storage medium containing machine-executable instructions for performing a method of validating a provided Social Security Number purported to be associated with a person, the machine-executable instructions comprising:
- a first set of machine-executable instructions for receiving the provided Social Security Number;
- a second set of machine-executable instructions for predicting a set of statistically probable Social Security Numbers;
- a third set of machine-executable instructions for comparing the provided Social Security Number to the set of statistically probable Social Security Numbers so as to determine a likelihood that the provided Social Security Number is legitimate;
- a fourth set of machine-executable instructions for communicating the likelihood to a reviewer; and
- a fifth set of machine-executable instructions for measuring the accuracy of the set of statistically probable Social Security Numbers using a legitimacy score, the legitimacy score including a parameter $1_1$ and a parameter $1_2$, further wherein:
  - $1_1$ is equal to $\alpha_1 r_{ANGN} + \alpha_2 r_{SN}$;
  - $1_2$ is equal to $\alpha_3 |A\check{N}/G\check{N} - AN/GN| + \alpha_4 |S\check{N} - SN|$;
  - $\alpha_{1,2,3,4}$ are functional weights;
  - $r_{ANGN}$ is a mean monthly Area Number and Group Number accuracy ratio of individuals born in the same month and state as a purported assignee;
  - $r_{SN}$ is a mean monthly Serial Number regression of individuals born in the same month and state as the purported assignee;
  - $A\check{N}/G\check{N}$ are predicted Area Number and Group Number values;
  - $S\check{N}$ is a predicted Serial Number values;
  - AN/GN are Area Number and Group Number values provided by the purported assignee; and
  - SN are Serial Number values provided by the purported assignee.

* * * * *